(12) United States Patent
Boyne-Aitken

(10) Patent No.: US 7,232,424 B2
(45) Date of Patent: Jun. 19, 2007

(54) SYRINGE PUMP BEARING MECHANISM

(75) Inventor: David E. Boyne-Aitken, Southampton (GB)

(73) Assignee: Cardinal Health 303, Inc., San Diego, CA (US)

( * ) Notice: Subject to any disclaimer, the term of this patent is extended or adjusted under 35 U.S.C. 154(b) by 493 days.

(21) Appl. No.: 10/425,576

(22) Filed: Apr. 29, 2003

(65) Prior Publication Data
US 2004/0220526 A1   Nov. 4, 2004

(51) Int. Cl.
*A61M 37/00* (2006.01)
(52) U.S. Cl. .................... 604/154; 128/DIG. 1
(58) Field of Classification Search ............ 604/154, 604/155; 417/415, 557; 471/362; 128/DIG. 1
See application file for complete search history.

(56) References Cited

U.S. PATENT DOCUMENTS

| 2,627,270 A | * | 2/1953 | Glass ..................... 604/155 |
| 5,236,416 A | | 8/1993 | McDaniel et al. |
| 5,673,593 A | * | 10/1997 | Lafferty ................ 74/89.38 |
| 5,896,804 A | | 4/1999 | Kimura et al. |
| 5,928,197 A | * | 7/1999 | Niehoff ................ 604/155 |
| 6,428,509 B1 | | 8/2002 | Fielder |
| 6,645,177 B1 | * | 11/2003 | Shearn ................. 604/155 |
| 6,958,053 B1 | * | 10/2005 | Reilly .................. 604/154 |
| 2003/0233069 A1 | | 12/2003 | Gillespie, Jr. |

FOREIGN PATENT DOCUMENTS

GB    2 224 444 A    5/1990

* cited by examiner

*Primary Examiner*—Nicholas D. Lucchesi
*Assistant Examiner*—Catherine N. Witczak
(74) *Attorney, Agent, or Firm*—Fulwider Patton LLP

(57) ABSTRACT

A lead screw mounting system for a syringe pump in which a second end of a lead screw is located within a connection tube that connects a drive device engaged with the lead screw to a plunger drive head. A bearing mount having diverging bearing surfaces is formed at the second end of the lead screw and a bearing having a complementary inner shape is mounted to the bearing mount. The bearing is larger than the inner diameter of the connection tube and is in constant contact with the tube. During operation, the bearing tends to move up one or the other of the diverging bearing surfaces of the bearing mount depending on which direction the connection tube is moving over the bearing creating a wedge action. The bearing functions to keep the lead screw concentrically located within the connection tube thereby increasing flow uniformity of the syringe pump.

37 Claims, 4 Drawing Sheets

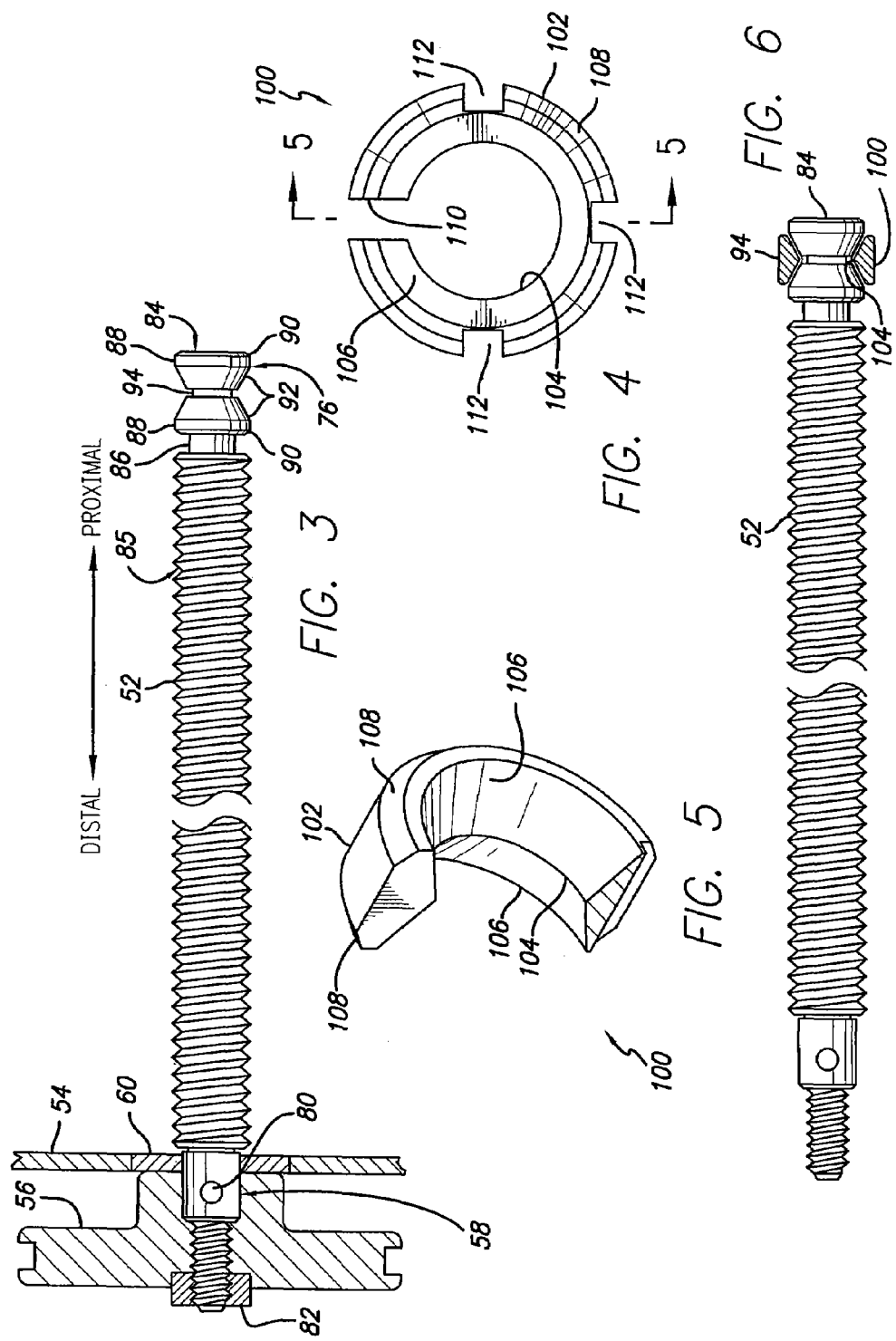

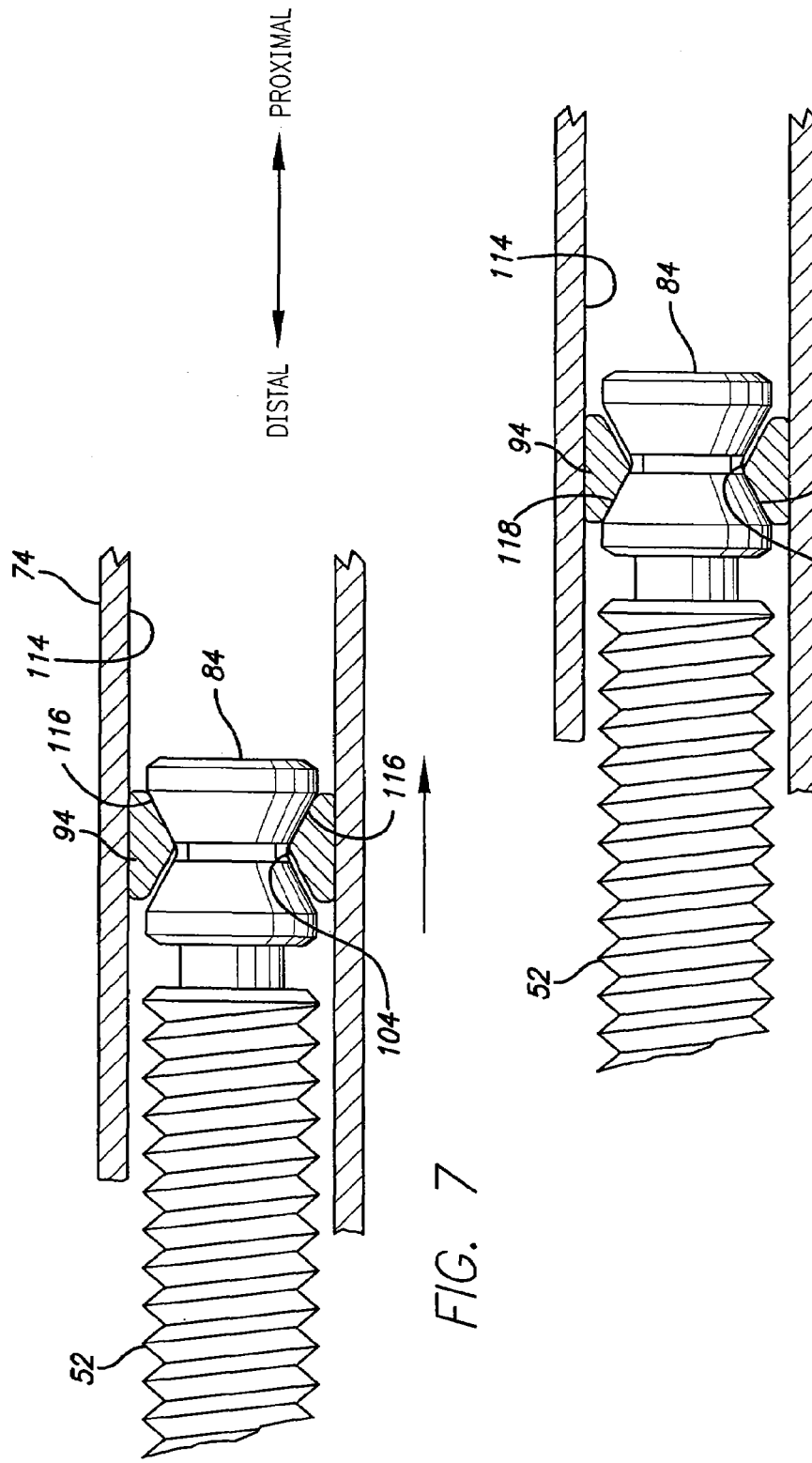

SYRINGE PUMP BEARING MECHANISM

BACKGROUND

The invention is related generally to lead screw drive mechanisms for medical infusion pumps, and more particularly, to a bearing system for mounting a lead screw in a syringe pump.

The infusion of fluids such as parenteral fluids into the human body is accomplished in many cases by means of a syringe pump having a lead screw and a screw drive device comprising a mechanism that translates the rotational motion of the lead screw into linear motion. The screw drive device is mounted to a syringe plunger driver head that typically grasps the plunger flange of a syringe and that applies the linear motion of the screw drive device to the syringe plunger to empty the syringe at a controlled rate.

Because syringes are of different lengths and are filled with different amounts of infusion fluids, the extension of the syringe plunger from the syringe barrel can differ from syringe to syringe. Many screw drive devices therefore include a disengagement mechanism that the operator uses to disengage the lead screw drive device from the lead screw threads. A disengagement mechanism control is typically located at the plunger driver head and can take the form of a lever or levers. Once disengaged, the operator may move the plunger driver head, and therefore the screw drive device to the position of the newly-mounted syringe plunger flange. The plunger driver head may then engage the syringe plunger flange and once engaged, the disengagement control may be released at which time the plunger driver head will grasp the plunger flange and the lead screw drive device will engage the threads of the lead screw at the new position. It is desirable that this disengagement mechanism and this plunger driver head be easy to use to facilitate operator usage of the pump.

Such a lead screw drive device with its integrated disengagement control and connected plunger driver head, although necessary, can impart substantial forces on almost any part of a lead screw. The screw drive device may be located at any position along the lead screw depending on the length of the syringe mounted for use and depending on the level of medical fluid remaining in the syringe. Additionally, certain medical fluids are more difficult to pump due to their viscosity or for other reasons, further placing an increased load on the lead screw. For these reasons, it is desirable to provide substantial mounting stability to the lead screw so that efficiency is maintained in the development of rotational movement, in the translation of that rotational movement to linear movement, and in the application of that linear movement to the syringe plunger head.

It is also the goal of syringe pump manufacturers to produce pumps having increased flow uniformity. That is, manufacturers strive to produce pumps that will pump exactly the selected flow rate throughout the infusion and not vary from that selected flow rate, until the syringe is exhausted or the rate is changed by the operator. However, mechanical tolerances of the syringe pump parts, interactions with the syringe, or other reasons can cause the flow rate of a syringe pump to vary from the selected rate. A variance from the prescribed and selected flow rate can be undesirable, especially if significant, in that the patient may not receive the desired level of the infusion fluid when needed. Manufacturers continue to refine their pump designs to reduce these variances in flow rate as much as possible.

In one lead screw arrangement, one end of the lead screw, i.e., a first end, is mounted through a transfer plate and has a pulley mounted to its end. The transfer plate forms a part of the inner frame of the syringe pump and consequently provides a stable and rigid mounting point for the lead screw. The lead screw pulley is directly engaged to the drive pulley of a motor through a drive belt. A bearing may surround the lead screw at the portion located through the transfer plate to lessen the effects of friction. In another arrangement, both the first end of the lead screw and the drive shaft of the motor may have gears and may be interconnected through an intermediate gear or gears, although this arrangement can result in less efficiency. In one design, the second end of the lead screw may also be mounted to a rigid plate with a bearing thus providing firm mounting to both ends of the lead screw. However, mounting the second end of the lead screw to a rigid mounting plate is not always an available option, especially when an extension tube must be used between the screw drive device and the plunger driver head.

The disengagement mechanism is typically formed as part of the drive device and permits selective engagement and disengagement of the drive device with the lead screw so that the drive device may be selectively positioned on the lead screw to accommodate different lengths of the syringes. A typical disengagement mechanism includes half-nuts that are spring loaded into contact with the threads of the lead screw. Through a series of levers and cams, the half-nuts may be moved outwards from engagement with the lead screw threads so that the drive device may be slid along the lead screw to the desired position. The length of the lead screw and the disengagement mechanism are designed to easily move the drive device along a substantial portion of the lead screw so that the smallest syringes and the largest syringes for which the pump is designed can be used with the pump.

In one particular design, the second end of the lead screw is located within a hollow connection tube that connects the screw drive device with the plunger driver head. The second end of the lead screw is not rigidly mounted but instead "floats" within the connection tube. The length of the lead screw is selected to exceed the travel of the syringe plunger within the syringe barrel so that syringes of various sizes may be accommodated. When the syringe barrel is full, the syringe plunger will be at the proximal end of the barrel with the plunger stem extended almost its entire length outside the syringe barrel. This configuration results in the overall syringe being almost twice the length of its barrel. Because some syringes are relatively long, the lead screw may be located at one end of the pump housing, for example the distal end, with the connection tube extending from the lead screw to a point near the other end of the housing, for example the proximal end, to engage the syringe plunger stem flange. However, the second end of the lead screw will always be located within the connection tube regardless of where the syringe plunger driver head is located.

In the approach described above where the second end of the lead screw is located within the hollow connection tube and is allowed to "float" in the tube, rigid mounting of that second end is not possible. Because there is a size difference between the outer diameter of the lead screw second end and the inner diameter of the hollow interior of the connection tube, the angle of the lead screw within the connection tube can change. Even a slight change in the angle between the two has been found to lessen the flow uniformity of the pump. The second lead screw end tends to move within the connection tube depending on the forces exerted on the lead screw thus adding inefficiency to the translation of the rotational motion of the lead screw to the linear motion of the screw drive device. The lead screw threads can change their angle of engagement with the screw drive device threads resulting in greater or lesser friction between the two and consequently resulting in lowered flow uniformity or flow accuracy of the pump.

A further undesirable effect of the floating second end of the lead screw is that it interacts with the interior of the connection tube scoring or gouging out the tube thereby imparting increased wear, and causing a larger difference in size between the lead screw and the connection tube thereby allowing for even more movement of the second end of the lead screw in the future.

In an effort to reduce the undesirable effects caused by movement of the floating lead screw, the floating second end of the lead screw has been hollowed to reduce its weight. This has been found to lessen the damage it does to the connection tube and can lower the amount of movement of the second end resulting in greater flow uniformity. However, the manufacturing process of hollowing a lead screw increases the cost of the screw as well as increases the rate of lead screw waste due to errors made during the hollowing process. This waste also increases manufacturing costs.

Hence, those skilled in the art have recognized a need for a stabilizing mechanism to be used with the second end of the lead screw so that the end is held in axial alignment with the connection tube and the drive device during operation. Further, those skilled in the art have recognized a need for reducing the costs of manufacturing a lead screw. The invention satisfies these needs and others.

SUMMARY OF THE INVENTION

The present invention is directed to a system and method for mounting the second end of a lead screw within an connection tube such that the lead screw is stabilized and aligned with the connection tube is maintained during the entire range of movement of the connection tube over the lead screw. The present invention also provides for changing the second end of a lead screw such that those lead screws previously found to be defective due to poor workmanship are now usable. Further, the invention provides for a lead screw that may be solid in configuration thus foregoing a manufacturing step of hollowing the screw thus reducing the cost of the lead screw.

In one aspect, the invention is directed to a syringe pump having a lead screw with a drive device in threaded engagement with the lead screw, the drive device moving along the lead screw in response to rotation of the lead screw, and a drive head adapted to drive a syringe plunger into the barrel of a syringe to expel fluid contents of the syringe, the syringe pump comprising a lead screw having a first end and a second end with the first end mounted to a frame, a connection tube located over the lead screw and connected between the drive device and the drive head to communicate movement of the drive device along the lead screw to the drive head, the connection tube having a hollow portion with an inner surface, wherein the second end of the lead screw is located within the hollow portion of the connection tube but is otherwise unmounted, and a bearing located at the second end of the lead screw in contact with the inner surface of the hollow portion of the connection tube thereby creating a guided cantilever mount of the second end of the lead screw within the connection tube.

In more detailed aspects, the second end of the lead screw comprises a bearing mount having outwardly diverging bearing surfaces with the bearing located at the bearing mount, the bearing engaging one or the other of the diverging bearing surfaces in response to movement of the connection tube over the bearing in a particular direction. In further aspects, the outwardly diverging mounting surfaces of the bearing mount diverge in axial directions from a bearing surface center location, the bearing engaging one or the other of the diverging mounting surfaces depending upon the direction of movement of the connection tube over the bearing. Further, the bearing mount has a generally hourglass shape.

In yet other aspects, the bearing has inner tapered surfaces for engaging the diverging bearing surfaces of the bearing mount and the bearing is biased outwardly into continuous contact with the inner surface of the connection tube. Further, the bearing has an inner surface that is shaped in an approximate complementary shape to the diverging bearing surfaces, whereby the bearing locates the second end of the lead screw in the approximate center of the connection tube.

Other detailed aspects include the bearing having a larger outer diameter than the inner diameter of the hollow portion of the connection tube within which it is mounted, the bearing having a discontinuity that permits the bearing to compress to thereby be mounted within the connection tube. Further, the bearing has a notch formed in an outer surface so that the bearing will bend at a desired location. In more detail, the bearing has a plurality of notches formed in the outer surface of the bearing so that the bearing will bend at desired locations to provide a more uniform force against both the bearing surfaces and the inner surface of the connection tube to more accurately locate the second end of the lead screw within the connection tube.

In yet other detailed aspects, the bearing and bearing surfaces of the bearing mount are made of materials selected such that the bearing easily slides along the bearing surfaces, whereby the bearing moves up one or the other bearing surfaces to maintain contact between the inner surface of the connection tube and the respective bearing surface to more accurately center the second end of the lead screw in the connection tube.

Other aspects and advantages of the invention will become apparent from the following detailed description and the accompanying drawings, illustrating by way of example the features of the invention.

BRIEF DESCRIPTION OF THE DRAWINGS

FIG. 3 presents a side view of an embodiment of a lead screw in accordance with aspects of the invention and as used in FIGS. 1 and 2 showing the first end mounted through a cross-sectioned transfer plate via a bearing with a drive pin, with the cross-sectioned drive pulley shown mounted to the first end of the lead screw via a mounting nut, and the second end of the lead screw having an "hour glass" shaped bearing mount, or bearing race, for mounting a bearing;

FIG. 4 is a side view of a bearing in accordance with aspects of the invention usable with the bearing mount located at the second end of the lead screw of FIG. 3, to stabilize the second end of the lead screw within the connection tube of FIG. 2, showing the split of the bearing, a plurality of slots in the external surface of the bearing, and the inner bearing tapers for engagement with the bearing mount;

FIG. 5 is a perspective view of a cutaway portion of the bearing of FIG. 4 along lines 5—5 showing the inner profile that mates with the hourglass shape of the bearing mount (race) located at the second end of the lead screw, and the external bearing surface that mates with the inner surface of the connection tube;

FIG. 6 is an assembled view of the bearing at the second end of the lead screw of FIG. 3 in accordance with aspects of the invention, with the bearing of FIGS. 4 and 5 in place on the bearing mount, showing the bearing in cross section;

FIG. 7 shows the bearing in contact with the inner surface of the connection tube, the bearing also in contact with the proximal diverging surface of the bearing mount due to movement of the connection tube in the proximal direction; and FIG. 8 again shows the bearing in contact with the inner surface of the connection tube, the bearing in this case being in contact with the distal diverging surface of the bearing mount due to movement of the connection tube in the distal direction.

DETAILED DESCRIPTION OF PREFERRED EMBODIMENTS

Figure 1:
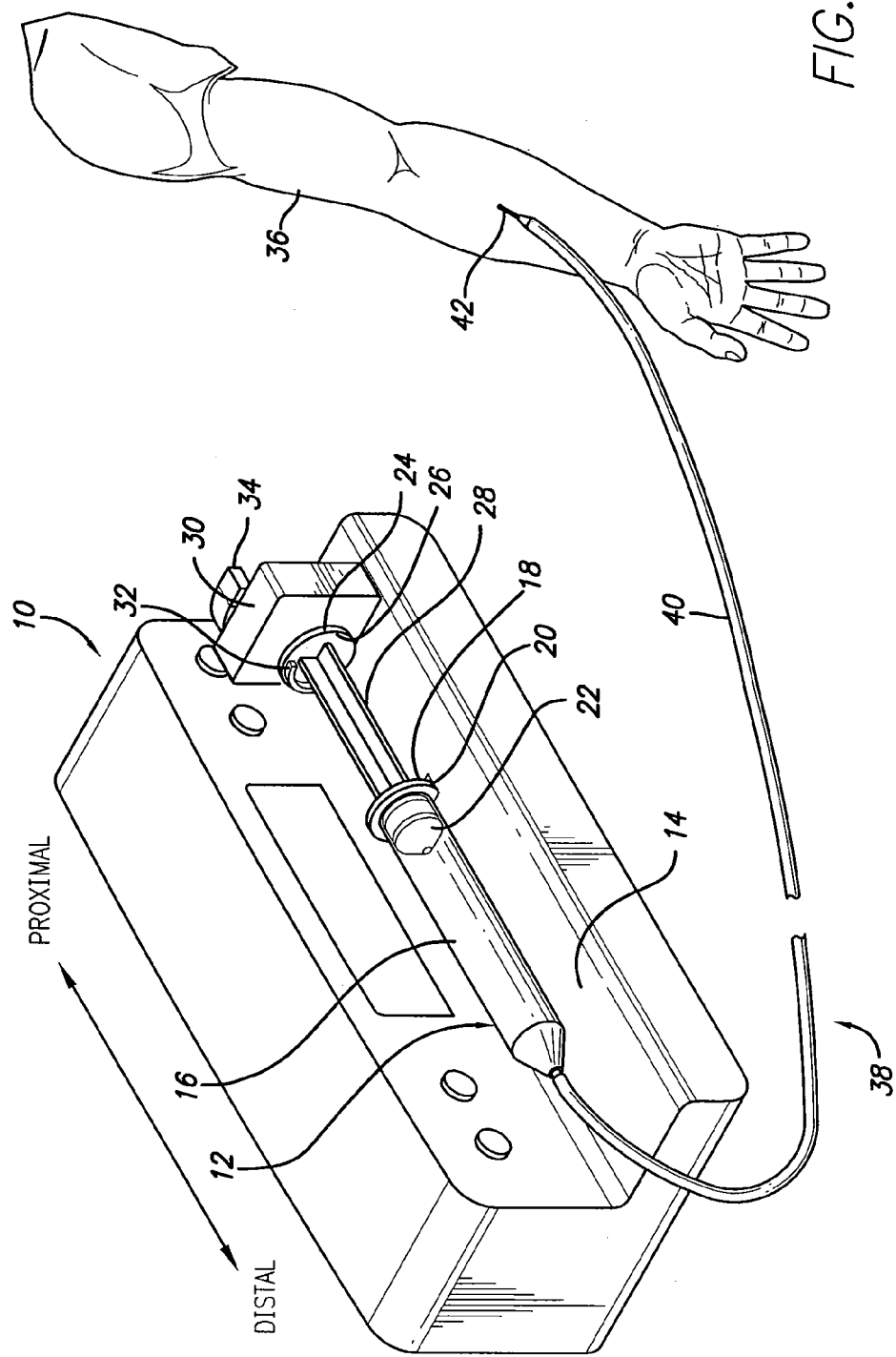
FIG. 1 is a perspective view of a syringe pump showing a syringe mounted on the pump for use in infusing its contents to a patient through a medical fluid administration set, a drive head in contact with the syringe plunger flange to drive the syringe plunger into the syringe barrel to expel the contents of the syringe into the fluid administration set that is connected to the vascular system of a patient.

Referring now to the drawings with more particularity, wherein like reference numerals designate like or corresponding elements among the several views, there is shown in FIG. 1 a view of a syringe pump 10 having a plunger driver system in accordance with the principles of the invention. A syringe 12 is shown mounted in the pump with certain mounting and sensing details removed for clarity of illustration. The syringe pump includes a syringe cradle 14 in which the syringe barrel 16 will rest. The syringe barrel flange 18 will be located in a barrel flange groove 20 in the pump 10 to immobilize the syringe barrel from longitudinal movement during movement of the syringe plunger 22 within the barrel.

Details of the barrel flange groove are not shown in FIG. 1 nor are they described here since such a feature is well known to those skilled in the art. Additionally, the function of the groove in holding a syringe barrel longitudinally immobile may be provided by different structure than that shown. Further a barrel clamp typically is also used to retain the syringe barrel at its position in the syringe pump, but is not shown here in order to preserve the clarity of other features.

The syringe plunger flange 24, having an inner side 26, is interconnected with the syringe plunger 22 by a syringe plunger stem 28. When mounted in the syringe pump 10 properly, the plunger flange 24 is held at a plunger drive head 30 with a pair of pivotally mounted plunger retaining arms 32, one of which is shown in the closed position in FIG. 1. The second pivotally mounted arm has been removed for clarity purposes. A disengagement lever 34 is used to disengage the plunger drive head 30 from the threads of a lead screw (not shown) as well as control the positions of the retaining arms 32 to allow removal and insertion of a syringe plunger flange 24. Disengaging the plunger drive head 30 from the threads of the lead screw permits the operator to move the plunger drive head 30 along the lead screw to the correct position to capture the plunger flange of a syringe 12. As is well known and as is described in the BACKGROUND section, syringes 12 having different quantities of fluid in them may be provided for use with a syringe pump 10 and the plunger 22 may be located at different positions in relation to the barrel 16. Additionally, syringes of different sizes may be usable in the syringe pump 10, which also results in the plunger flange 24 being at different locations, depending on the size of the syringe and the level to which it is filled. The ability to manually move the drive head 30 permits the accommodation of syringes of different sizes with different beginning plunger positions.

From the foregoing, it will be appreciated that the plunger driver system as shown and described provides a versatile system to accept various sizes of syringes and results in easier pump operation as well as resists siphoning. For further details on a drive head with a disengagement lever and flange-grasping arms, refer to U.S. Pat. No. 6,428,509 to Fielder, issued on Aug. 6, 2002, which is hereby incorporated by reference.

Returning to FIG. 1, the syringe 12 is connected to a patient 36 through a fluid administration set 38 comprising a length of tubing 40. The tubing 40 is mounted to a sharpened cannula 42 that has been introduced to a blood vessel of the patient 36. As the drive head 30 moves in the distal direction, fluid residing in the syringe barrel will be expelled into the tubing 40 of the fluid administration set 38 and flow into the patient's vein through the cannula 42. It should be noted that the administration set 38 may have additional features, such as a pressure sensor disk, flow controllers, ports, or other devices mounted to it or formed as part of it. Such devices have not been shown in this figure so as to maintain clarity of illustration of the basic administration set.

Figure 2:
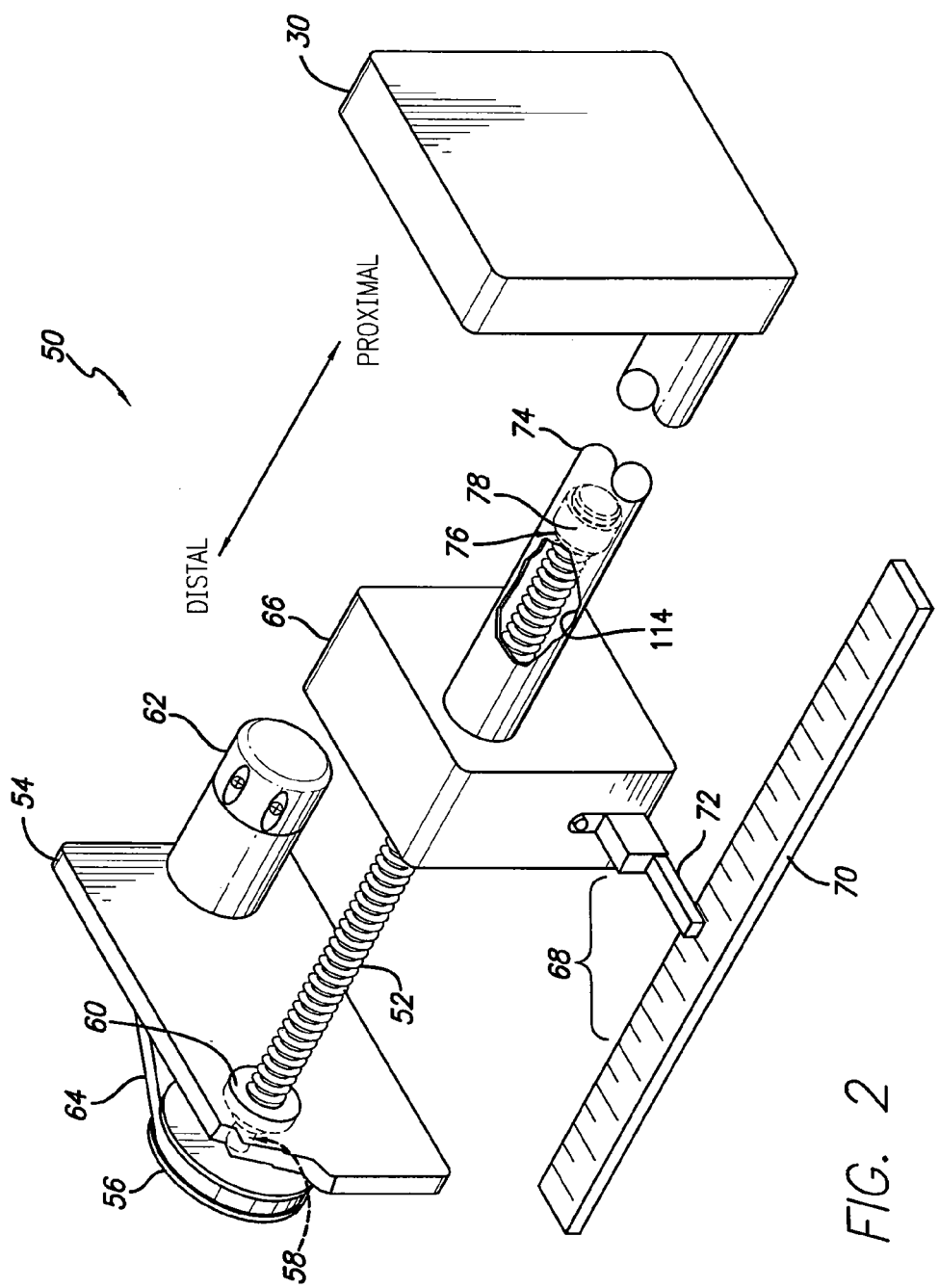
FIG. 2 is a simplified perspective view of the drive device of the syringe pump of FIG. 1 in which a lead screw is mounted at a first end through a transfer plate and has a pulley for drive connection with a motor, the lead screw having a floating second end located within an connection tube that connects a drive device engaged with the threads of the lead screw with the drive head shown in FIG. 1.

FIG. 2 presents further details of a syringe pump drive assembly 50 showing a threaded lead screw 52 mounted to a transfer plate 54. The transfer plate forms part of the internal frame of the syringe pump, its anchored nature providing a rigid mounting point for the first end of the lead screw. A corner of the transfer plate 54 has been cut away so that a drive pulley 56 mounted to a first end 58 of the lead screw can be more clearly seen. The first end 58 is mounted within a first bearing 60 for providing a lower friction mounting arrangement with the transfer plate 54. In this case, the first bearing has been welded to the transfer plate to achieve a permanent mounting. A drive motor 62 is also mounted to the transfer plate 54 and includes a motor pulley (not shown) on the other side of the transfer plate. A drive belt 64 interconnects the motor pulley with the drive pulley 56 and transfers rotary movement developed by the motor to the drive pulley 56 and thereby, to the lead screw 52. Different arrangements of coupling the rotary motion of the motor to the lead screw may be used, including a direct drive arrangement or a series of gears. Efficiencies may vary depending on the particular drive arrangement chosen.

A screw drive device 66 is mounted to the lead screw 52 and, although not shown, is prevented from rotating due to its mounting arrangement in the syringe pump. Such mounting arrangements are well known to those skilled in the art and hence, no further details are provided here. It therefore will translate the rotation of the lead screw to linear motion. Because the lead screw is firmly anchored in the syringe pump and can only rotate, the drive device will move along the lead screw. An optical position determination system 68 is shown comprising a set or markers 70 with an optical reading device 72. The optical position determination system may also be capable of determining the speed of movement of the drive device 66 based on the time between sensing various markers. Such a position-determination and speed-of-movement system is known to those skilled in the art and no further details are provided here. U.S. Pat. No. 5,236,416 to McDaniel, issued on Aug. 17, 1993 describes such a system and is incorporated herein by reference. Other designs and mechanisms may be used to accomplish the same result.

The screw drive device 66 is connected to the plunger drive head 30 that was shown in FIG. 1 with a hollow connection tube 74. The connection tube is firmly mounted to the screw drive device 66 and to the drive head 30. Thus, linear movement of the screw drive device along the lead screw causes the drive head to move commensurately. Such a system is known to those skilled in the art and no further details are provided herein. U.K. Patent No. GB 2 224 444 to Welmed Limited, inventor B. Lim, published May 9, 1990, describes and shows such a drive arrangement and is incorporated herein by reference.

It will be noted by reference to FIG. 2 that the lead screw 52 resides partially within the connection tube 74 and has a second end 76 located fully within the connection tube. In accordance with the previous description, the drive device 66 moves along the lead screw as the lead screw rotates. Further, the drive device can be manually located anywhere along the lead screw so that the drive head 30 may engage a mounted syringe plunger flange (seen in FIG. 1). For example, when a large syringe is mounted to the syringe pump and that syringe is full, the drive head 30 may need to be moved much farther to the right in the figure (proximal direction), in which case, less of the lead screw will reside within the connection tube. As the lead screw is rotated by the motor 62 to move the drive head 30 to the left direction (distal) in the figure to empty the syringe, more of the lead screw will be located within the connection tube. In all cases, the second end 76 of the lead screw will always be located within the connection tube.

To overcome some of the problems facing prior syringe pump drive devices as previously reviewed, the second end 76 of the lead screw 52 in the embodiments shown includes a connection tube bearing 78 in accordance with aspects of the invention. The bearing is configured to make contact with the inner surface of the connection tube to keep the second end 76 of the lead screw better centered within the connection tube 74. Other than the bearing, the second end of the lead screw is unmounted. The lead screw is thus generally in a cantilever arrangement; however, the addition of the bearing that contacts both the lead screw second end and the inner surface of the connection tube results in a "guided cantilever mounting" of the second end of the lead screw. This "guided" mounting has been found to result in the lead screw constantly being concentric with the connection tube which greatly improves flow uniformity of the syringe pump.

Referring to FIG. 3, a side view of the lead screw 52 is shown. The transfer plate 54, lead screw pulley 56, and the first bearing 60 are shown. As mentioned above, in a preferred embodiment the first bearing 60 is welded to the transfer plate; however, it may be press fit or held in place through other means. The pulley 56 may be mounted to the lead screw in various well known ways. In this case, the pulley has a drive pin 80 that assures rotation of the pulley with the rotation of the lead screw 52, and a retaining nut 82 that affixes the pulley to the first end 58 of the lead screw. Other mounting techniques for both the bearing and the pulley are possible.

At the second end, or proximal end 76, of the lead screw 52, a bearing mount 84 or bearing race is formed. Formed at a location proximal to the threads 85 and between the threads and the bearing mount is a thread undercut 86. The bearing mount has a land 88 at each end with outer chamfers 90. The outer chamfers facilitate sliding the bearing mount into the connection tube. The bearing mount also comprises two outwardly diverging bearing surfaces 92 separated by a bearing mount undercut 94. The bearing mount 84 has the general appearance of the shape of an hourglass. The bearing mount undercut 94 is a production feature providing a convenient place in which the bearing may be compressed during the process of sliding the second end 76 of the lead screw into the connection tube 74. The crest of the bearing, as is shown and described below, will be located at least initially in the undercut 94 and because of the depth of the undercut, bearings of differing sizes may function well in the bearing mount 84. This permits the bearings to be made with looser tolerances which reduces manufacturing costs.

A suitable lead screw bearing 100 in accordance with aspects of the invention is shown in FIGS. 4 and 5. The bearing comprises an outer bearing surface 102, an inner bearing crest 104, two tapered surfaces 106, and chamfers 108 on either side of the outer bearing surface. The bearing is split 110 as shown in FIG. 4 to allow the bearing to be more easily mounted over the bearing mount 84. Three slots 112 are also formed in the outer bearing surface to control the points of bending of the bearing. Because the slots are spaced at ninety degrees from each other, including the split 110, the bearing more uniformly applies outward pressure to the connection tube, which provides better centering action of the lead screw within the connection tube. The three notches 112 and the split 110 have the effect of producing four segments with a more controlled spring effect as well as making the bearing easier to compress when inserting it into the connection tube 74. Although three notches are shown in this embodiment, more or fewer notches may be used as desired.

In FIG. 6, the bearing 100 is shown mounted to the bearing mount 84 of the lead screw 52. The crest 104 of the bearing is located within the bearing mount undercut 94 of the bearing mount which provides a good starting position for the bearing. It will be noted from the figure that when centered on the bearing mount, the bearing inner diameter is larger than the outer diameter of the corresponding points of the bearing mount 84 and the outer diameter of the bearing is larger than the outer diameter of the threads of the lead screw 52. This is so that the outer surface of the bearing will always make contact with the inner surface 114 of the connection tube 74 (FIG. 2). The connection tube is typically formed by injection molding and because of that process, the inner channel 114 through the connection tube is tapered from one end to the other. Consequently the lead screw bearing 78 must be able to accommodate the tapering inner diameter of the connection tube. Hence, the outer diameter of the lead screw bearing is set so that it will make contact with the largest inner diameter of the connection tube. The chamfers 108 of the bearing 78 shown in FIG. 4 assist in mounting the second end 76 of the lead screw within the connection tube 74. Whether the second end of the lead screw is pushed forward into the connection tube or drawn rearward into the connection tube, the outer chamfers provide an angle of contact between the bearing and the ends of the connection tube that tend to compress the bearing so that insertion into the connection tube is facilitated. Additionally, the chamfers remove any sharp edges of the bearing that may have otherwise provided greater friction with the inner surface of the connection tube once the bearing is mounted within the connection tube.

Additionally, the bearing 78 tapered surfaces 106 are complementary to the diverging surfaces 92 of the bearing mount 84. Because the bearing 100 is formed of a low friction substance, it will easily slide along the diverging surfaces 92 of the bearing mount as needed to maintain the lead screw second end 78 centered within the connection tube 74. The diverging surfaces 92 of the bearing mount give the mount a general hourglass appearance. It can also be noted that the bearing mount 84 is symmetric about the bearing mount under cut 94 and this shape provides a distinct advantage, as is demonstrated in FIGS. 7 and 8.

Referring now to FIG. 7, the bearing 100 and bearing mount 84 located at the second end 76 of the lead screw 52 are shown mounted within the connection tube 74, which is partially shown. The bearing is in contact with the inner surface 114 of the connection tube. Because the connection tube is being drawn in the proximal direction, possibly because the drive head 30 is being attached to a new syringe (FIG. 1), the friction between the bearing outer surface 102 and the inner surface 114 of the connection tube draws the bearing up the proximal diverging surface 116 of the bearing mount in a "wedging" action. Because the tapered bearing surfaces 106 have the same angle as the diverging bearing surfaces 92 of the bearing mount 84, an inclined plane type of arrangement results. This wedging action has the effect of providing even more stabilizing force against the lead screw to keep it centered within the connection tube.

FIG. 8 presents another condition in which the connection tube 74 is being moved over the second end 76 of the lead screw 52, this time in the distal direction. This is probably due to the syringe pump 10 being operated to expel the contents of the syringe 12 into the administration set 38 (FIG. 1). Consequently, the drive head 30 and connection tube 74 are moving toward the syringe barrel 16, in the distal direction. Because the connection tube is being drawn in the distal direction, the friction between the bearing outer surface 102 and the inner surface 114 of the connection tube draws the bearing up the most distal diverging surface 118 of the bearing mount in the wedging action described above. As also mentioned, this wedging action has the effect of providing even more stabilizing force against the lead screw to keep it centered within the connection tube, and in this case where medical fluid is being infused into the patient, this centering action has been found to result in better flow uniformity from the syringe pump.

This wedging action results because the bearing 100 is larger than the inner diameter of the connection tube 74 and consequently exerts a continual force against the interior of the connection tube, and because of the friction between the inner surface 114 of the connection tube and the outer surface 102 of the bearing. Additionally, the diverging surfaces 92 of the bearing mount 84 and the complementary tapered surfaces 106 of the bearing 100 facilitate movement of the bearing into the wedging action.

The lead screw may be formed of stainless steel with an electroless nickel plate. The bearing may be formed of Delrin™ material, an acetal resin available from E.I. DuPont de Nemours and Company. The connection tube may be formed of glass-filled nylon. Other materials may be used for these components as well.

While in the present embodiment, the bearing mount is cut from the same piece of material as the threaded portion of the lead screw, other approaches are possible. For example, in the case where hollowed lead screws exist, the bearing mount may be made separately and attached to the proximal end of the lead screw, such as by adhesive or welding thereby salvaging lead screws or possibly providing a lower cost lead screw.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

What is claimed is:

1. A syringe pump having a lead screw with a drive device in threaded engagement with the lead screw, the drive device moving along the lead screw in response to rotation of the lead screw, and a drive head adapted to drive a syringe plunger into the barrel of a syringe to expel fluid contents of the syringe, the syringe pump comprising:
   a lead screw having a first end and a second end with the first end mounted to a frame, the second end of the lead screw comprises a bearing mount having outwardly diverging bearing surfaces;
   a connection tube located over the lead screw and connected between the drive device and the drive head to communicate movement of the drive device along the lead screw to the drive head, the connection tube having a hollow portion with an inner surface;
   wherein the second end of the lead screw is located within the hollow portion of the connection tube but is otherwise unmounted; and
   a bearing located at the bearing mount in contact with the inner surface of the hollow portion of the connection tube thereby creating a guided cantilever mount of the second end of the lead screw within the connection tube.

2. The syringe pump of claim 1 wherein:
   the bearing engaging one or the other of the diverging bearing surfaces in response to movement of the connection tube over the bearing in a particular direction.

3. The syringe pump of claim 2 wherein the outwardly diverging bearing surfaces of the bearing mount diverge outwardly in axial directions from a bearing surface center location, the bearing engaging one or the other of the diverging bearing surfaces depending upon the direction of movement of the connection tube over the bearing.

4. The syringe pump of claim 2 wherein the bearing mount has a generally hourglass shape.

5. The syringe pump of claim 2 wherein the bearing has inner tapered surfaces for engaging the diverging bearing surfaces of the bearing mount.

6. The syringe pump of claim 1 wherein the bearing is biased outwardly into continuous contact with the inner surface of the connection tube.

7. The syringe pump of claim 6 wherein
   the bearing engaging one or the other of the diverging surfaces in response to movement of the connection tube over the bearing in a particular direction; and
   the bearing has an inner surface that is shaped in an approximate complementary shape to the diverging bearing surfaces;
   whereby the bearing locates the second end of the lead screw in the approximate center of the connection tube.

8. The syringe pump of claim 2 wherein:
   the bearing and bearing surfaces of the bearing mount are made of materials selected such that the bearing easily slides along the bearing surfaces;

whereby the bearing moves up one or the other bearing surfaces to maintain contact between the inner surface of the connection tube and the respective bearing surface to more accurately center the second end of the lead screw in the connection tube.

9. The syringe pump of claim 8 wherein the bearing mount has a generally hourglass shape.

10. The syringe pump of claim 8 wherein the bearing has inner tapered surfaces for engaging the diverging bearing surfaces of the bearing mount.

11. The syringe pump of claim 1 wherein the bearing has a larger outer diameter than the inner diameter of the hollow portion of the connection tube within which it is mounted, the bearing having a discontinuity that permits the bearing to compress to thereby be mounted within the connection tube.

12. The syringe pump of claim 11 wherein the bearing has a notch formed in an outer surface so that the bearing will bend at a desired location.

13. The syringe pump of claim 11 wherein the bearing has a plurality of notches formed in the outer surface of the bearing so that the bearing will bend at desired locations to provide a more uniform force against both the bearing surfaces and the inner surface of the connection tube to more accurately locate the second end of the lead screw within the connection tube.

14. A syringe pump having a lead screw with a drive device in threaded engagement with the lead screw, the drive device moving along the lead screw in response to rotation of the lead screw, and a drive head adapted to drive a syringe plunger into the barrel of a syringe to expel fluid contents of the syringe, the syringe pump comprising:
   a lead screw having a first end and a second end with the first end mounted to a frame;
   a connection tube located over the lead screw and connected between the drive device and the drive head to communicate movement of the drive device along the lead screw to the drive head, the connection tube having a hollow portion with an inner surface;
   wherein the second end of the lead screw is located within the hollow portion of the connection tube but is otherwise unmounted; and
   a bearing located at the second end of the lead screw in contact with the inner surface of the hollow portion of the connection tube thereby creating a guided cantilever mount of the second end of the lead screw within the connection tube;
   wherein the bearing has a larger outer diameter than the inner diameter of the hollow portion of the connection tube within which it is mounted, the bearing having a discontinuity that permits the bearing to compress to thereby be mounted within the connection tube.

15. The syringe pump of claim 14 wherein the bearing has a notch formed in an outer surface so that the bearing will bend at a desired location.

16. The syringe pump of claim 14 wherein the bearing has a plurality of notches formed in an outer surface of the bearing so that the bearing will bend at desired locations to provide a more uniform force against both the bearing surfaces and the inner surface of the connection tube to more accurately locate the second end of the lead screw within the connection tube.

17. The syringe pump of claim 14 wherein the outwardly diverging bearing surfaces of the bearing mount diverge outwardly in axial directions from a bearing surface center location, the bearing engaging one or the other of the diverging bearing surfaces depending upon the direction of movement of the connection tube over the bearing.

18. The syringe pump of claim 14 wherein the bearing mount has a generally hourglass shape.

19. The syringe pump of claim 14 wherein the bearing has inner tapered surfaces for engaging the diverging bearing surfaces of the bearing mount.

20. The syringe pump of claim 14 wherein the bearing is biased outwardly into continuous contact with the inner surface of the connection tube.

21. The syringe pump of claim 20 wherein the second end of the lead screw comprises a bearing mount having outwardly diverging bearing surfaces;
   the bearing is located at the bearing mount, the bearing engaging one or the other of the diverging surfaces in response to movement of the connection tube over the bearing in a particular direction; and
   the bearing has an inner surface that is shaped in an approximate complementary shape to the diverging bearing surfaces;
   whereby the bearing locates the second end of the lead screw in the approximate center of the connection tube.

22. A syringe pump having a lead screw, a nut device engaged with the lead screw that moves along the lead screw in response to rotation of the lead screw, and a drive head adapted to drive a syringe plunger into a syringe barrel, the syringe pump comprising:
   a hollow connection tube located over the lead screw and connected between the nut device and the drive head such that movement of the nut device along the lead screw is communicated by the connection tube to the drive head, the connection tube having an inner surface;
   wherein the lead screw is mounted at a first end to a frame;
   wherein a second end of the lead screw is continuously located within the hollow connection tube and comprises a bearing mount having outwardly diverging bearing surfaces; and
   a bearing located at the bearing mount, the bearing configured to engage the bearing surfaces of the bearing mount and the inner surface of the connection tube so as to centrally locate the second end of the lead screw in the connection tube during movement of the connection tube along the lead screw.

23. The syringe pump of claim 22 wherein the bearing is biased outwardly into contact with the inner surface of the connection tube and wherein the bearing engages one or the other bearing surface depending on which direction the connection tube is moving over the lead screw.

24. The syringe pump of claim 22 wherein the bearing has a larger outer diameter than an inner diameter of the connection tube within which it is mounted, the bearing having a discontinuity that permits the bearing to compress to thereby be mounted within the connection tube.

25. The syringe pump of claim 22 wherein the bearing has a notch formed in an outer surface so that the bearing will flex at a desired location.

26. The syringe pump of claim 22 wherein the bearing has a plurality of notches formed in the outer surface of the bearing so that the bearing will flex at desired locations.

27. The syringe pump of claim 22 wherein the bearing has inner tapered surfaces for engaging the diverging bearing surfaces of the bearing mount.

28. The syringe pump of claim 22 wherein the outwardly diverging bearing surfaces of the bearing mount diverge outwardly in axial directions from a bearing surface center location, the bearing engaging one or the other of the diverging bearing surfaces depending upon the direction of movement of the connection tube over the bearing.

29. The syringe pump of claim 22 wherein the bearing mount has a generally hourglass shape.

30. The syringe pump of claim 22 wherein:
the bearing has an inner surface that is shaped in an approximate complementary shape to the diverging bearing surfaces;
whereby the bearing locates the second end of the lead screw in the approximate center of the connection tube.

31. A lead screw mounting system for use in a syringe pump having a drive head adapted to drive a syringe plunger into the barrel of a syringe to expel fluid from the barrel, the lead screw mounting system comprising:
a lead screw mounted at a first end to a frame;
a nut device engaged with the lead screw that moves along the lead screw in response to rotation of the lead screw;
a hollow connection tube located over the lead screw and connected between the nut device and the drive head such that movement of the nut device causes movement of the connection tube over the lead screw and causes movement of the drive head, the connection tube having an inner surface;
wherein a second end of the lead screw is continuously located within the hollow of the connection tube;
wherein the second end of the lead screw comprises a bearing mount; and
a bearing located at the bearing mount, the bearing having at least one tapered inner surface engaging the bearing mount and an outer surface engaging the inner surface of the connection tube so as to centrally locate the second end of the lead screw in the connection tube during movement of the connection tube along the lead screw.

32. The lead screw mounting system of claim 31 wherein the bearing is biased outwardly into contact with the inner surface of the connection tube.

33. The lead screw mounting system of claim 31 wherein the bearing mount comprises two diverging mounting surfaces, the bearing engaging one or the other depending upon the direction of movement of the connection tube over the bearing.

34. The syringe pump of claim 31 wherein the bearing includes a bearing surface center location and outwardly diverging bearing surfaces that diverge outwardly in axial directions from the bearing surface center location, the at least one tapered inner surface bearing engaging the diverging bearing surfaces.

35. The syringe pump of claim 31 wherein the bearing has a larger outer diameter than the inner diameter of the hollow portion of the connection tube with which it is engaged, the bearing having a discontinuity that permits the bearing to compress to thereby be mounted within the connection tube.

36. The syringe pump of claim 35 wherein the bearing has a notch formed in the outer surface so that the bearing will bend at a desired location.

37. The syringe pump of claim 35 wherein the bearing has a plurality of notches formed in the outer surface of the bearing so that the bearing will bend at desired locations to provide a more uniform force against both the bearing and the inner surface of the connection tube to more accurately locate the second end of the lead screw within the connection tube.

* * * * *